United States Patent
Neeman et al.

(10) Patent No.: US 9,788,916 B2
(45) Date of Patent: Oct. 17, 2017

(54) GUIDED DRILL, KIT OF GUIDED DRILLS AND METHODS OF OSTEOTOMY FOR INSERTING A DENTAL IMPLANT USING THE KIT

(71) Applicant: MIS Implants Technologies Ltd., Doar-Na Misgav (IL)

(72) Inventors: Asaf Neeman, Amirim (IL); Thaer Sliman, Akko (IL)

(73) Assignee: MIS Implants Technologies Ltd., Doar-Na Misgav (IL)

( * ) Notice: Subject to any disclaimer, the term of this patent is extended or adjusted under 35 U.S.C. 154(b) by 112 days.

(21) Appl. No.: 14/561,040

(22) Filed: Dec. 4, 2014

(65) Prior Publication Data

US 2015/0182298 A1    Jul. 2, 2015

Related U.S. Application Data

(60) Provisional application No. 61/911,494, filed on Dec. 4, 2013.

(51) Int. Cl.
*A61C 3/00* (2006.01)
*A61C 1/08* (2006.01)
*A61C 8/00* (2006.01)
*A61C 19/02* (2006.01)

(52) U.S. Cl.
CPC ............ *A61C 1/084* (2013.01); *A61C 8/0089* (2013.01); *A61C 19/02* (2013.01)

(58) Field of Classification Search
CPC ........ A61C 1/084; A61C 8/0089; A61C 19/02
USPC ............... 433/75, 72, 76, 172, 174, 165
See application file for complete search history.

(56) References Cited

U.S. PATENT DOCUMENTS

| | | | | |
|---|---|---|---|---|
| 2002/0172923 A1* | 11/2002 | Strong | ............... | A46B 3/005 433/102 |
| 2003/0049586 A1* | 3/2003 | Kumar | ............ | A61C 8/0089 433/165 |
| 2011/0306009 A1* | 12/2011 | Suttin | ............... | A61C 1/084 433/75 |

* cited by examiner

*Primary Examiner* — Michael Carey
(74) *Attorney, Agent, or Firm* — Rodney J. Fuller; Booth Udall Fuller, PLC

(57) ABSTRACT

A guided drill for osteotomy for a dental implant is provided. The guided drill includes a guide body configured to fit within a guide sleeve attached to a surgical template. A surgical kit includes a series of guided drills with each guided drill having a different combination of a drilling diameter and a drilling length, a container containing the series of guided drills in a form of an array, and a chart comprising a map of the array and graphical indications. The graphical indications are configured to indicate to a user of the surgical kit a suggested order of sequentially using the series of guided drills from the array to perform a part of osteotomy procedure and obtain a hole, having a prescribed diameter and a prescribed length, for a dental implant.

21 Claims, 15 Drawing Sheets

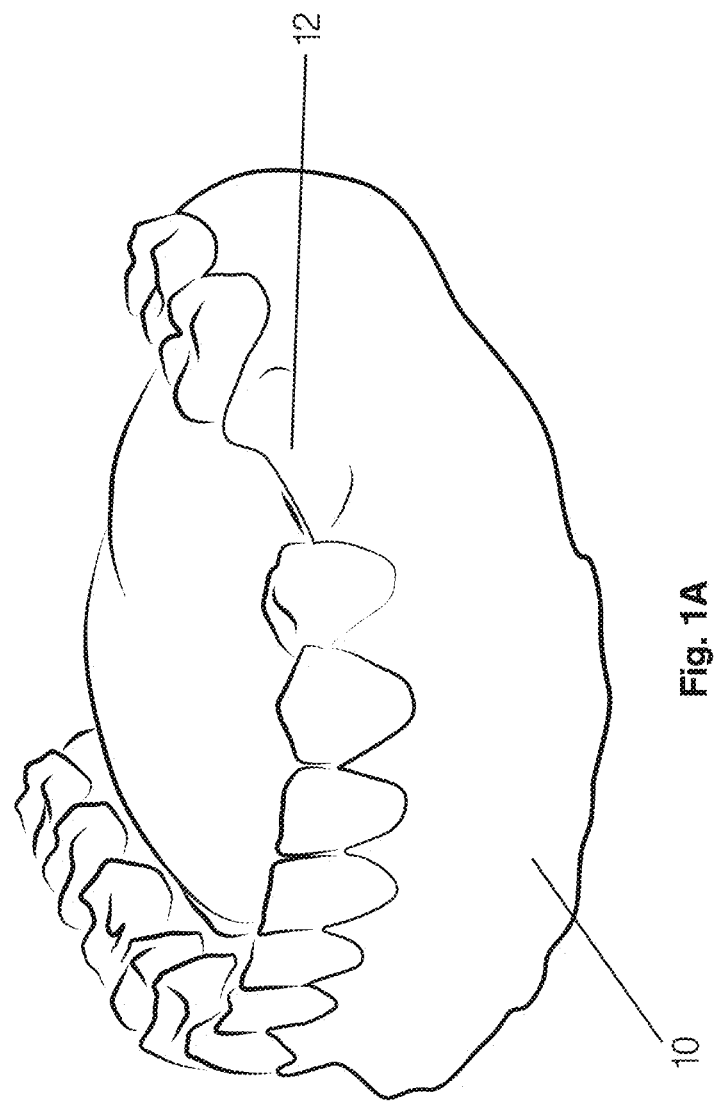

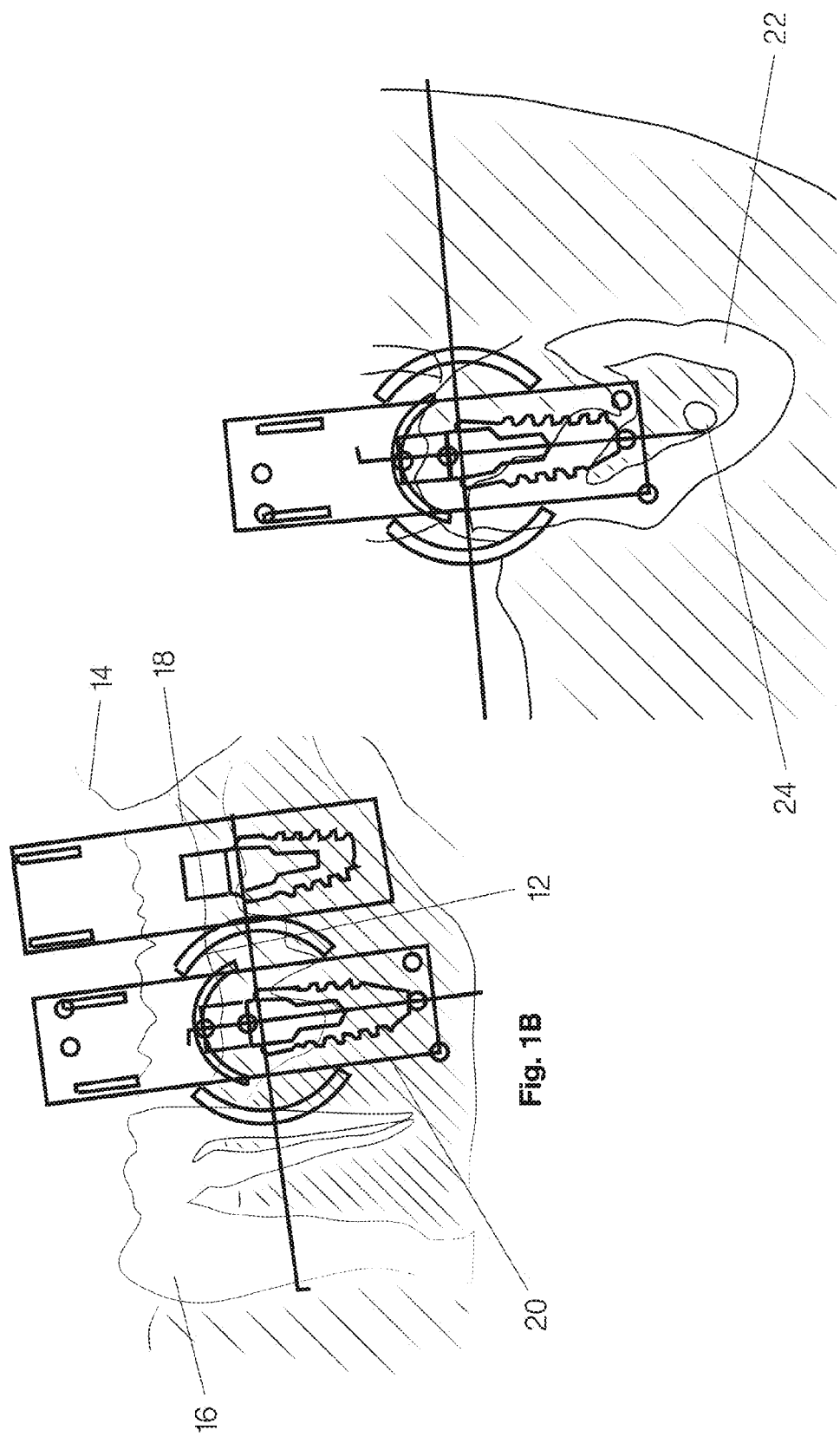

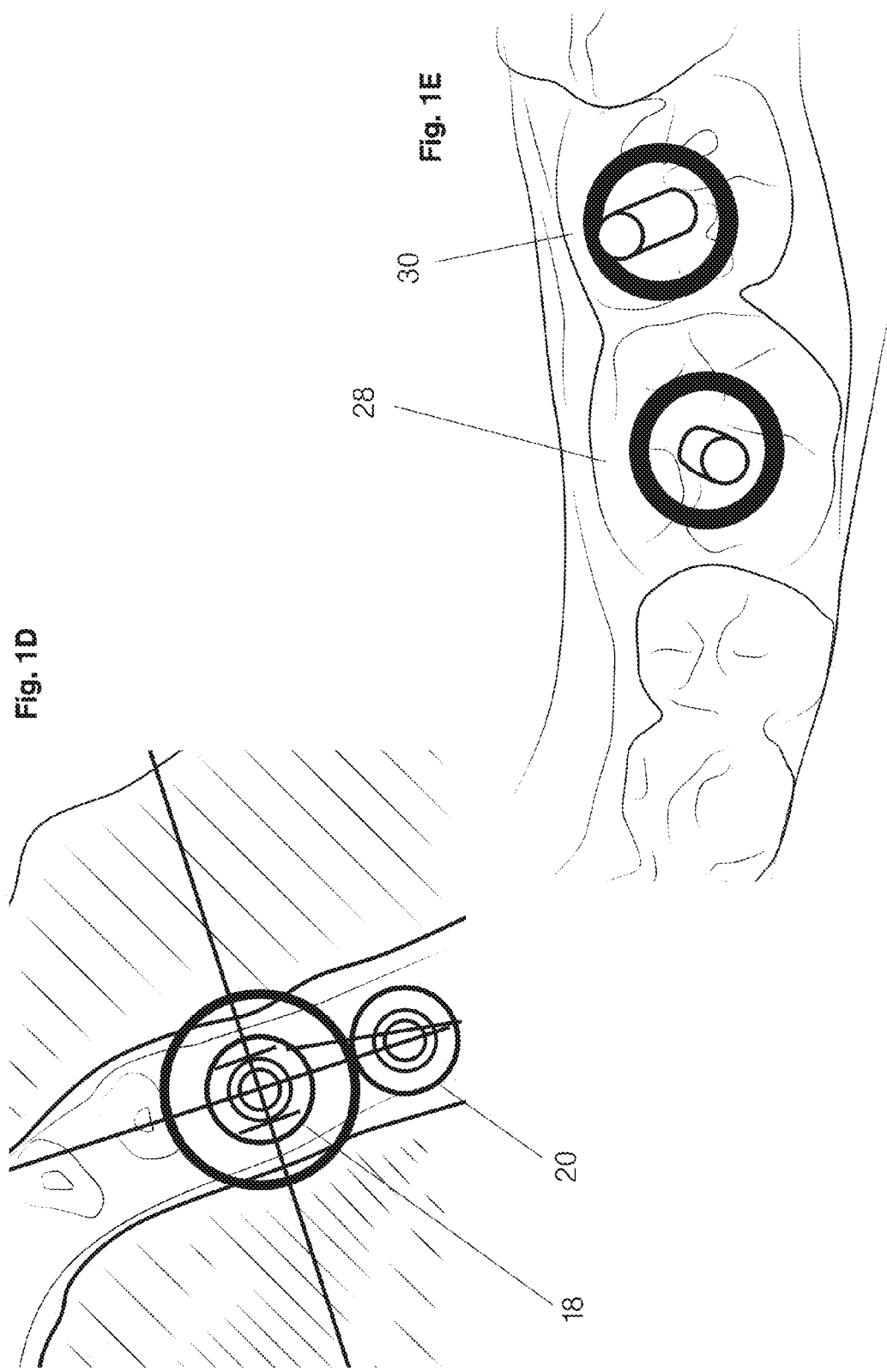

VIEW F

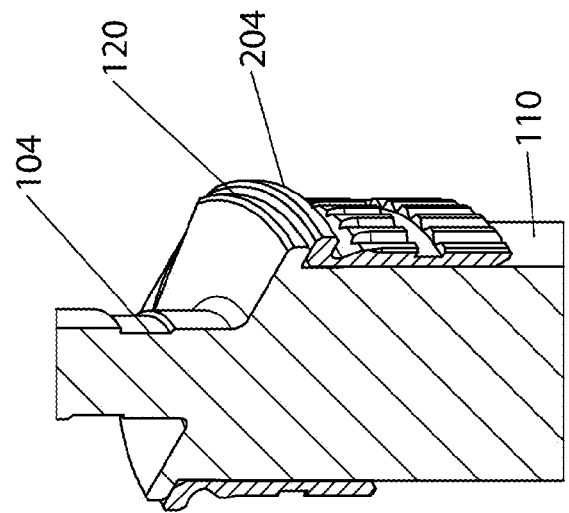
Fig. 2I
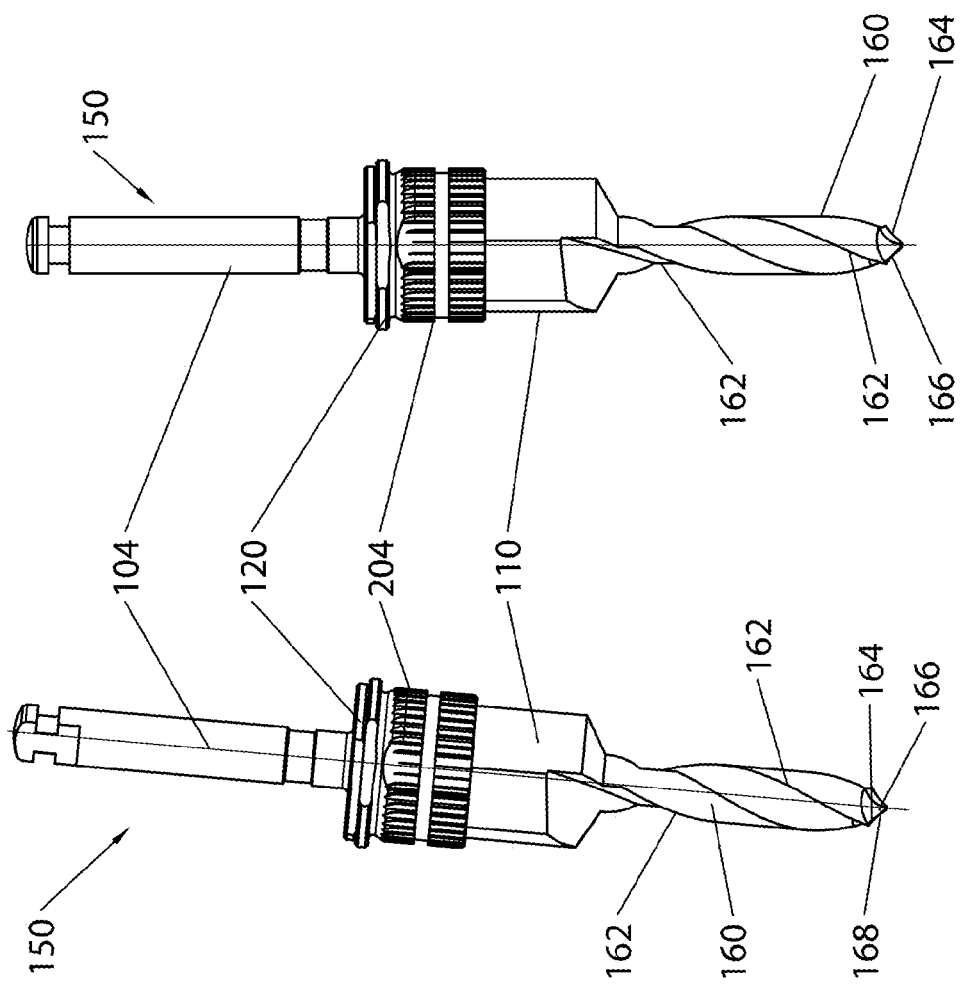
Fig. 2H
Fig. 2G

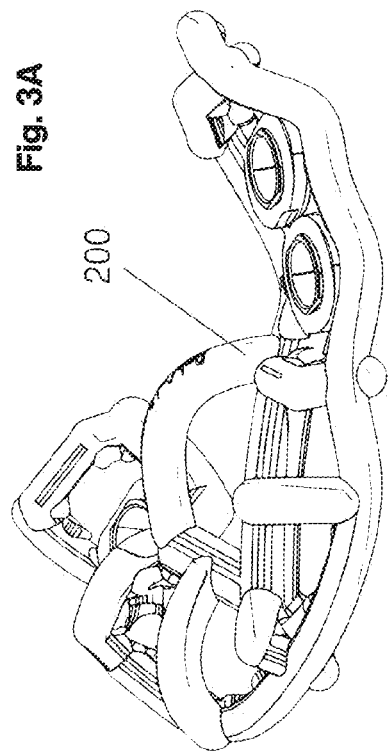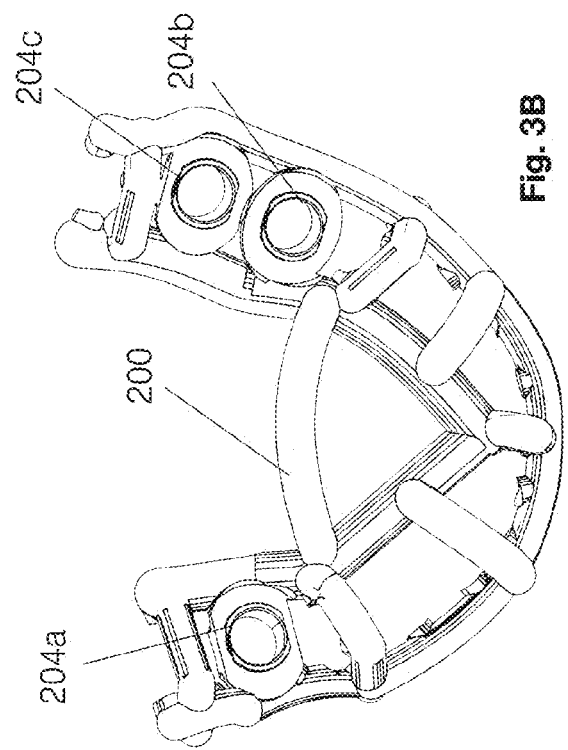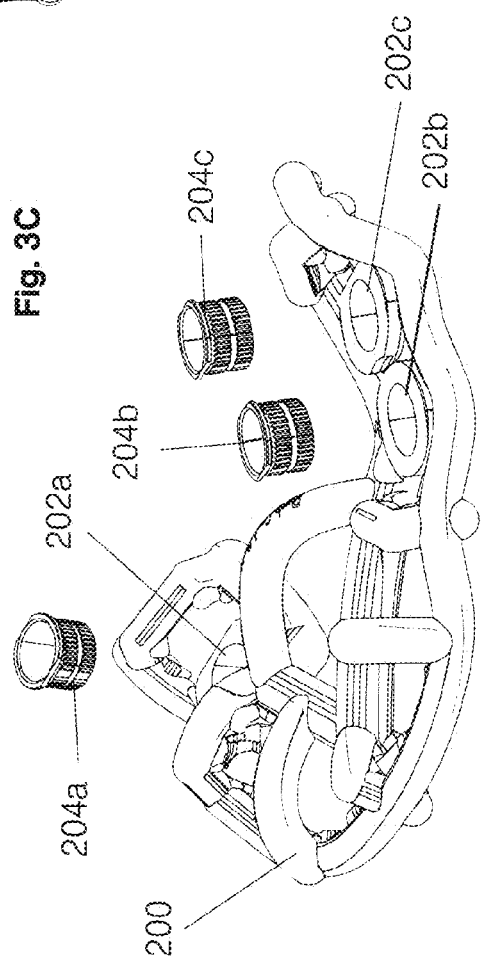

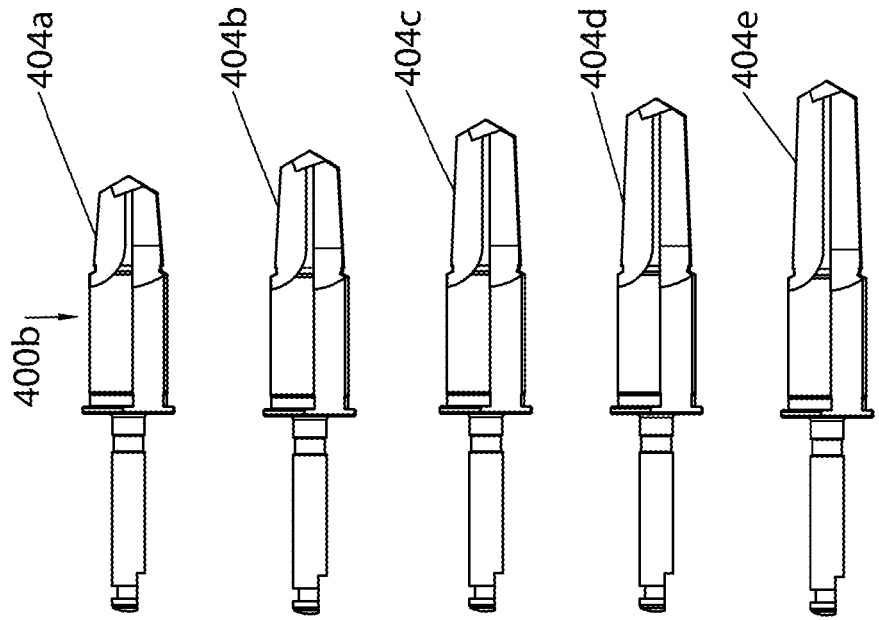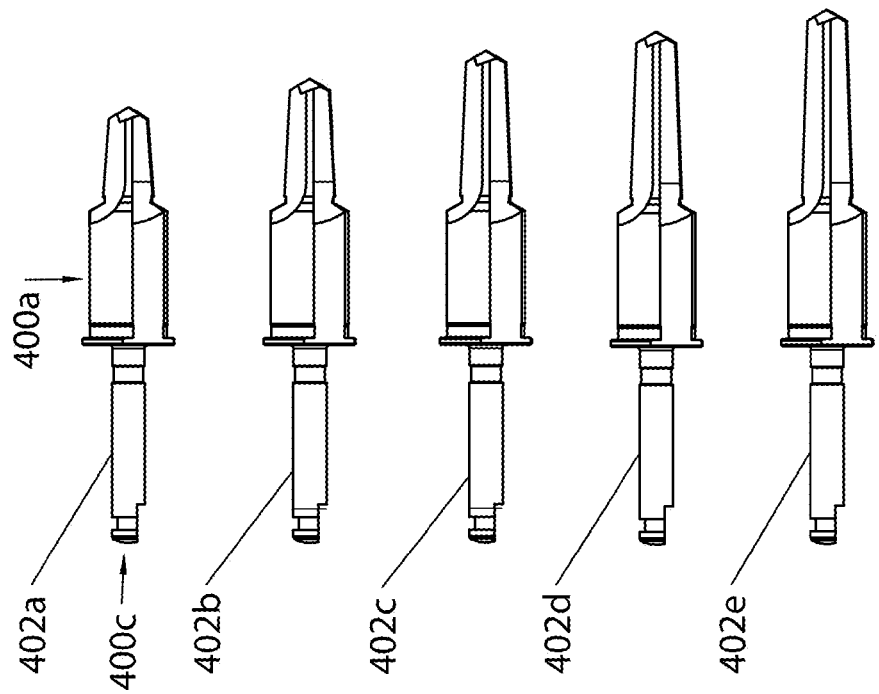
Fig. 4

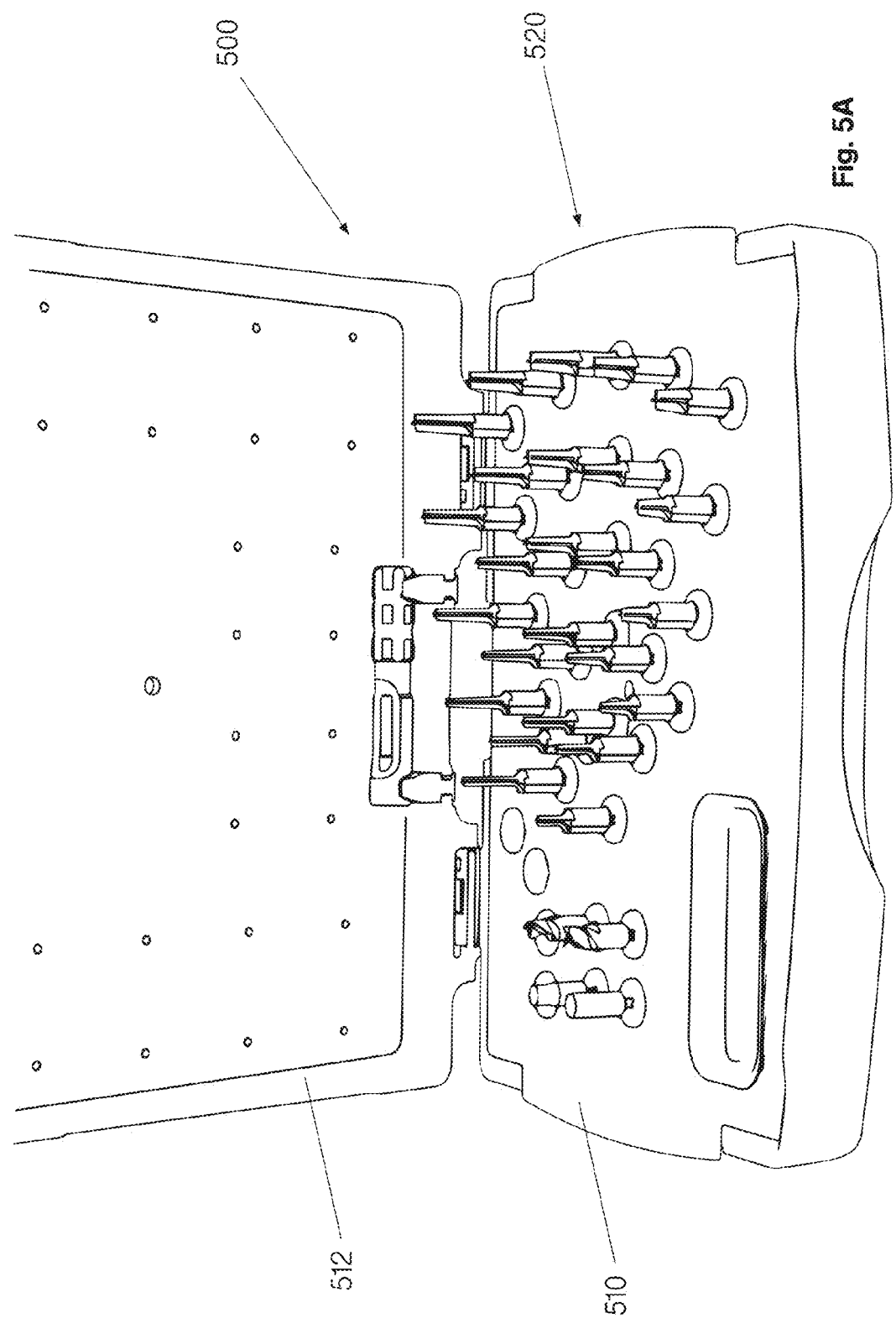

GUIDED DRILL, KIT OF GUIDED DRILLS AND METHODS OF OSTEOTOMY FOR INSERTING A DENTAL IMPLANT USING THE KIT

CROSS-REFERENCE TO RELATED APPLICATIONS

This application claims the benefit of U.S. Provisional Application No. 61/911,494, filed Dec. 4, 2013, the contents of which are expressly incorporated by reference in its entirety.

TECHNICAL FIELD AND BACKGROUND

The disclosure, in some embodiments, relates to the field of dental osteotomy, and more particularly, but not exclusively, to a guided drill and guided drilling for inserting dental implants.

SUMMARY

Guided osteotomy surgery is becoming a preferred option for insertion a dental implant. According to some techniques of guided osteotomy (sometimes referred to as guided implant surgery), a preferred site for inserting an implant in a jaw of a patient is selected, and the course of the surgery is pre-planned, during a procedure or a set of procedures preceding the surgery possibly by days or weeks. Following the completion of the plan of the surgery, the surgeon is provided with means for guiding the surgical acts to the desired surgery site at high accuracy, as is further exemplified herein below.

An exemplary method for planning a guided implant surgery is described in FIGS. 1A-1G. FIG. 1A schematically depicts a lower jaw 10 of a patient in need for two dental implants in an implant region 12. An impression of the jaw may be obtained and a physical model of the jaw, made of e.g. plastic or plaster, is constructed, using any suitable technique known in the art. Also, a virtual 3D model of the jaw is obtained and stored in a computer, e.g. by scanning the 3D physical model of the jaw using a computerized image acquiring device such as a CCD camera and a suitable virtual model constructing software.

A suitable technique of radiological imaging, such as X-ray computed tomography (CT), particularly cone-beam CT (CBCT), may be employed to obtain a 3D image of the bones and tissues of the jaw, particularly around the implant region. A qualified personal such as a clinician, e.g. a dentist, may then plane and select an osteotomy site for the implants. According to some techniques the dental clinician may use a dedicated software to view the 3D image of bones and tissues, and to virtually insert an implant to the bone, on that 3D image. FIG. 1B schematically depicts a portion of a 3D X-ray image obtained using CBCT, of the implant region 12, in sagital view. The implant region is seen between existing tooth 14 and existing tooth 16. Virtual implant representations 18 and 20 of two implants are positioned on the image and the clinician is enabled to displace each implant representation and orient it on the image so as to select a preferred location and a preferred orientation for the implant in the bone. FIG. 1C schematically depicts the implant region in a frontal view, showing the position of implant representation 20 relative to bone 22 of the jaw, and particularly relative to mandibular nerve 24. In addition to selecting a preferred position—location and orientation—for the implants, the clinician may select a preferred combination of a length and a diameter for the implants, so as to optimally fit anatomical characteristics of the jaw and the implant region. After a suitable implant, having a desired combination of length and diameter, is selected, a drilling program, comprising a drilling sequence, may be planned. Such a drilling program may often be dependent on additional anatomical data of the patient, such as bone density and/or bone hardness. It is noted that some such anatomical data may not be known completely or accurately enough, before the surgery actually begins.

FIG. 1D schematically depicts implant representation 18 and implant representation 20 on the X-ray image in axial view. FIG. 1E schematically depicts a virtual image of artificial teeth 28 and 30, virtually positioned on the image of the jaw in conjunction with the position of the implants representations 18 and 20, respectively.

According to some techniques, guiding the surgeon to accurately drill in a planned osteotomy site is achieved using a guide sleeve, having a cylindrical hollow shape, which is fixedly positioned relative to the osteotomy site. A drill is passed through the guide sleeve, the guide sleeve being positioned and oriented so that the drill accurately drills in the planned osteotomy site. According to some embodiments, fixedly positioning a guide sleeve relative to the osteotomy site may be obtained using a personalized surgical template as is described below.

The surgical template may be designed using a dedicated design software and by considering a virtual 3D model of the jaw and teeth of the patient. FIG. 1F schematically depicts a 3D virtual model of a surgical template 40, virtually attached to a 3D virtual model of the lower jaw of the patient. The surgical template, schematically depicted in FIG. 1G, may be manufactured, e.g. by 3D printing, from a tough material such as a hard polymer material or it may be manufactured from metal such as titanium using other techniques, e.g. electron-beam melting. The surgical template is constructed to be mechanically fixed relative to the teeth of the patient during an osteotomy procedure. According to some embodiments the surgical template may be mechanically fit to the teeth of the patient so as to grip onto the teeth, when attached to the teeth in a pre-defined mutual orientation between the teeth and the surgical template. Additionally or alternatively the surgical template may be mechanically fit and attached to the gingiva of the patient or to provisional implants already fixed in the jaw, or the surgical template may be mechanically fit and attached to another organ or a body part with a fixed (substantially rigid) spatial relationship with the osteotomy site.

Surgical template 40 comprises two housings, 42 and 44, respectively, each housing houses a guide sleeve (not shown in this Figure), typically made of titanium. During an osteotomy procedure the surgical template is properly attached to the teeth of the patient in the pre-planned mutual orientation between the teeth and the surgical template, and grips thereto. When the surgical template is so attached to the teeth, each guide sleeve in housings 42 and 44 is configured to guide a drill towards a respective osteotomy site.

According to some techniques employed during an osteotomy procedure, obtaining a hole in a bone of jaw, suitable for inserting a dental implant therein, is accomplished in several steps, using several different drills. To enable properly guiding different drills, generally having different diameters, through a same guide sleeve, an adapting ring or an adapting cylinder is ought to be used. According to some known techniques, a drill guidance key such as a drill adaptor or a drill spoon is used, comprising a handle having at one end a hollow cylinder having an outer diameter adapted to be inserted into the guide sleeve, and an inner diameter adapted to receive therein a drilling drill. In use, the handle is held by the surgeon or by an assistant as drilling is carried out. According to other known techniques, an adapting ring is attached onto a drill prior to drilling, so that during drilling the adapting ring is positioned substantially between the revolving drill and the guide sleeve.

It is noted that such known techniques as described above are less than optimal because of one or more of several reasons. Using an adapting part such as an adapting ring to compensate a mismatch between a diameter of the guide sleeve and a diameter of a drill introduces an additional tolerance, and therefore an increased inaccuracy, compared to drilling with a drill configured to slidingly revolve inside a guide sleeve without an adapting ring. Moreover, the use of an adapting part such as a drill guidance key or an adapting ring renders the drilling procedure more complex, more cumbersome and more time consuming. Further yet, the need to hold a drill guidance key during drilling often requires another person, in addition to the surgeon, to assist during surgery, which further complicates the procedure.

There is thus provided according to an aspect of some embodiments a guided drill for osteotomy for a dental implant, configured to drill by revolving around a revolution axis. The guided drill comprises a shank configured to be releasably mechanically associated with a contra angle hand piece, wherein the contra angle hand piece being configured to revolve the guided drill around the revolution axis. The guided drill further comprises a guide body having an outer surface geometrically confined by a cylinder having a radius R1 so that the outer surface coincides with the cylinder at least along an areal section thereof. The guided drill is thereby configured to slidingly revolve inside a guide sleeve having a hollow cylindrical shape with an inner radius R2 larger than R1, whereas the revolution axis coincides with a symmetry axis of the guide sleeve, so that the guided drill is constrained to displacements substantially along the revolution axis. The guided drill further comprises a stopper arranged between the shank and the guide body, the stopper extending radially to a distance greater than R1 from the revolution axis. The guided drill further comprises a blade portion configured for drilling at a diameter smaller than 2*R1, the blade portion arranged next to the guide body, so that the guide body is between the blade portion and the stopper. The shank, the stopper, the guide body and the blade portion are integrally formed together from a hard alloy. According to some embodiments, the blade portion comprises at least three straight cutting edges or at least two spiral cutting edges, wherein the cutting edges comprise reliefs, thereby rendering the guided drill reusable.

According to an aspect of some embodiments there is provided an osteotomy set. The osteotomy set comprises the guided drill described above and a surgical template constructed to mechanically fit to teeth in an upper jaw or in a lower jaw of a specific, named patient. The surgical template, when attached to the teeth of the patient in a pre-defined mutual orientation between the teeth and the surgical template, may grip onto the teeth, and is thereby substantially fixed thereto. The surgical template comprises a guide sleeve having a hollow cylindrical shape with an inner radius R2, wherein the guide sleeve is oriented, when the surgical template is properly attached to a patient's teeth, so as to enable passage of a guided drill therethrough towards an osteotomy site in the patient's jaw. The guide sleeve is thereby configured to guide a revolving guided drill, having a guide body confined within a radius R1 smaller than R2, towards the osteotomy site.

A procedure such as described above of guided osteotomy for drilling a hole in a bone for inserting a dental implant may in principal be formulated as a prescribed recipe for the surgeon, such as "use a guided drill with a drilling diameter of xx mm and a drilling length of yy mm to drill the hole for a dental implant" (according to some techniques a few guided drills may be used sequentially until the last drill in the series obtains a hole with the required, pre-defined dimensions). However, in practice, such a pre-defined, prescribed recipe for performing the osteotomy procedure might be unfavorable and even detrimental due to characteristics that are unknown during the planning stage of the procedure. Such characteristics may be for example anatomic data of the patient, which are not revealed during the preparation stages—for example such data that are not revealed by X-ray images and that the surgeon reveals only during the procedure. For example, in a hypothetical case, a pre-planned program of the surgery may include drilling a 3.2 mm diameter hole for inserting a 3.3 diameter implant. While carrying out the procedure the surgeon may reveal that the bone of the patient is not a hard bone but a soft bone, and the surgeon consequently may decide that for inserting a 3.3 mm diameter implant, a 2.4 mm hole should be drilled in a soft bone. In a different hypothetical case the surgeon may decide, while performing the osteotomy procedure, that the planned depth of the hole might not suffice for supporting an implant, and that increasing the depth by e.g. 1.5 mm or 2 mm (according to available drills) may be both safe for the jaw and the patient and also beneficial for longevity of the implant.

According to an aspect of some embodiments there is thus provided a series of the guided drills described above, wherein the guide bodies in all the guided drills in the series are geometrically confined to a same cylinder with a same radius R1. Each guided drill in the series provides a combination of a drilling diameter and a drilling length different from a combination of a drilling diameter and a drilling length provided by another guided drill in the series. The series is thereby configured to allow a user of the series of guided drills, such as a maxillofacial surgeon, to perform, using the series, part of an osteotomy procedure for a dental implant at a drilling diameter and a drilling length which are decided upon by the maxillofacial surgeon during the osteotomy procedure. Using guided drills from series of guided drills, all having a guide body with a same radius greatly facilitates the procedure for the user of the guided drills as it enables the user to replace one guided drill with a successive guided drill quickly and efficiently, whereas all the guided drills are guided by a same guided sleeve to the osteotomy site. No adapting element such as an adapting ring is required, no tunable device or tunable component is required to be tuned and no assistance is required to hold an adapting device such as a drill guidance key.

According to some embodiments there is thus provided an osteotomy set comprising the surgical template described hereinabove and the series of guided drills according to the teachings herein.

According to an aspect of some embodiments there is provided a surgical kit comprising the series of guided drills as described above. The surgical kit further comprises a container configured to contain at least the series of guided drills. The container has an open state wherein the series of guided drills are visible and accessible to a user. In the open state the series of guided drills are arranged in an array according to at least one of the drilling diameter and drilling length of each guided drill. Next to each guided drill in the array, having a specified drilling diameter and a specified drilling length, is disposed another guided drill having a successive drilling diameter or a successive drilling length in the series of guided drills. The surgical kit further comprises a chart comprising a map of the array, and graphical indications. The graphical indications are configured to indicate to a user of the surgical kit a suggested order of sequentially using a sub-series of the series of guided drills to perform a part of an osteotomy procedure, thereby obtaining a hole having a prescribed diameter and a prescribed length, for a dental implant.

According to an aspect of some embodiments there is further provided a method of osteotomy for a dental implant. The method may comprise:

(a) providing a surgical kit as described above;
(b) following the chart of the osteotomy kit, selecting a first guided drill and drilling a first drill in an osteotomy site in a bone of a patient's jaw;
(c) following the chart of the surgical kit, selecting a next guided drill and drilling a next drill in a bone of a patient's jaw, and
(d) repeating step (c) as many times an desired by a user of the surgical kit.

The first guided drill may be utilized as a pilot drill. "First guided drill", "pilot drill" and "starter guided drill" may be used herein interchangeably.

According to some embodiments the method may further comprise:

providing a surgical template substantially as described herein above, configured to fit and attach to teeth of the patient, whereas a guide sleeve of the surgical template is oriented so as to guide a guided drill towards the osteotomy site, and passing a drilling guided drill through the guide sleeve of the surgical template so that during drilling in steps (b) and (c), the guide body of the guided drill slidingly revolves inside the guide sleeve, thereby guiding the guided drills to drill in the osteotomy site, to a prescribed drilling depth.

According to some embodiments the method may further comprise, following step (b) collecting anatomic data of the patient, and considering the anatomic for selecting a next guided drill in step (c).

According to some embodiments the anatomic data may comprise bone hardness and/or bone density.

There is separately provided herein a guided drill which can be used for guided osteotomy for dental implant.

There is separately provided herein a guided drill which can be used, together with a surgical template having a suitable guide sleeve, for guided osteotomy for dental implant.

There is separately provided herein a reusable guided drill which can be used for repeating guided osteotomy surgeries for dental implant.

There is separately provided herein one series or more of reusable guided drills which can enable a user of the series of guided drills to perform, using the series, osteotomy for a dental implant at a drilling diameter and a drilling length which are decided upon by the user during the osteotomy procedure.

There is separately provided herein an array of guided drills, which can facilitate an osteotomy procedure and enhance efficiency of carrying out the same.

There is separately provided herein a chart comprising a map of the array, which can be used for indicating to a user about a suggested order of sequentially using guided drills from the array obtain a hole, having a prescribed diameter and a prescribed length, for a dental implant.

Certain embodiments of the present disclosure may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

Unless otherwise defined, all technical and scientific terms used herein have the same meaning as commonly understood by one of ordinary skill in the art to which this invention pertains. In case of conflict, the patent specification, including definitions, takes precedence.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise.

BRIEF DESCRIPTION OF THE FIGURES

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures:

FIG. 1A schematically depicts a lower jaw of a patient in need for two dental implants in an implant region;

FIG. 1B schematically depicts a portion of a 3D X-ray image including the implant region of FIG. 1A, and two virtual implant representations positioned therein, in sagital view;

FIG. 1C schematically depicts a portion of a 3D X-ray image including the implant region of FIG. 1A, and a virtual implant representation positioned therein, in frontal view;

FIG. 1D schematically depicts a portion of a 3D X-ray image including the implant region of FIG. 1A, and a two virtual implant representations positioned therein, in axial view;

FIG. 1E schematically depicts a virtual image of artificial teeth, virtually positioned on the image of the jaw of FIG. 1A, in conjunction with the position of the implants representations of FIGS. 1B-1D;

FIG. 2G schematically depicts an embodiment of a guided drill according to an aspect of some embodiments, passing through a guide sleeve, in a perspective view;

FIG. 2H schematically depicts the guided drill and guide sleeve of FIG. 2G in front view;

FIG. 2I schematically depicts the guided drill and guide sleeve of FIG. 2G in a blown-up, cross-section view;

FIG. 3A schematically depict an embodiment of a surgical template according to an aspect of the invention, in a perspective view;

FIG. 3B schematically depict the surgical template of FIG. 3A in top view;

FIG. 3C schematically depict the surgical template of FIG. 3A in an exploded view;

FIG. 4 schematically depicts series of guided drills such as the guided drill of FIG. 2A;

FIG. 5A schematically depicts an embodiment of a surgical kit, comprising an array of guided drills and a chart, for assisting in drilling a hole in a bone of a patient's jaw, in perspective;

DESCRIPTION OF SOME EMBODIMENTS

Figure 1F:
FIG. 1F schematically depicts a 3D virtual model of a surgical template, virtually attached to a 3D virtual model of the lower jaw of FIG. 1A.
Figure 1G:
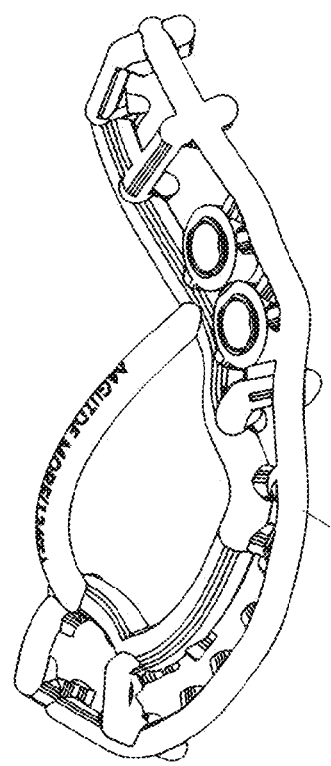
FIG. 1G schematically depicts the surgical template of FIG. 1F.

The principles, uses and implementations of the teachings herein may be better understood with reference to the accompanying description and figures. Upon perusal of the description and figures present herein, one skilled in the art is able to implement the invention without undue effort or experimentation. In the figures, like reference numerals refer to like parts throughout.

Before explaining at least one embodiment in detail, it is to be understood that the invention is not necessarily limited in its application to the details of construction and the arrangement of the components and/or methods set forth herein. The invention is capable of Other embodiments or of being practiced or carried out in various ways. The phraseology and terminology employed herein are for descriptive purpose and should not be regarded as limiting.

Figure 2A:
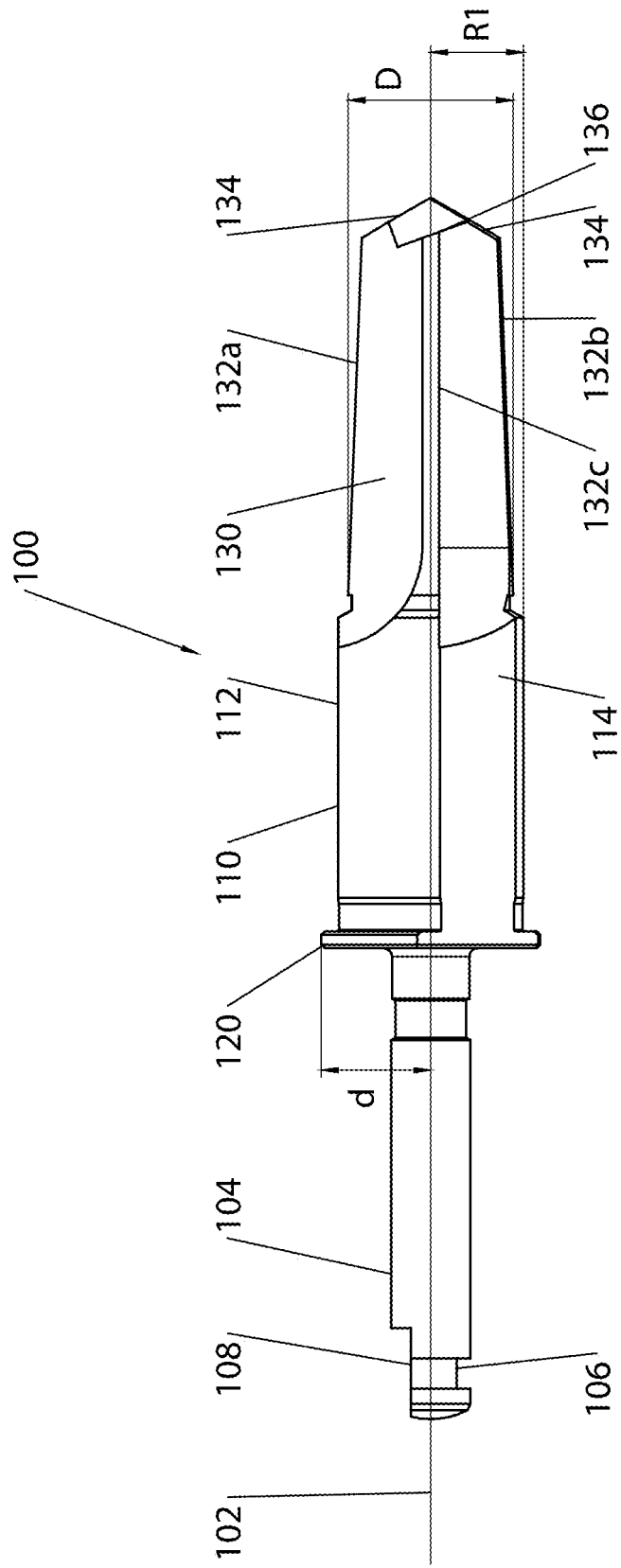
FIG. 2A schematically depicts an embodiment of a guided drill according to the teachings herein.

FIG. 2A schematically depicts an embodiment of a guided drill 100, configured to drill by revolving around a revolution axis 102, for performing osteotomy for inserting a dental implant. The guided drill comprises a shank 104 configured to be releasably mechanically associated with a contra angle hand piece (not shown), wherein the contra angle hand piece being configured to revolve the guided drill around the revolution axis 102. The shank is generally shaped as a long cylinder extending along the revolution axis and having a ring shaped recess 106 and planar recess 108, configured to enable a suitable grip of the guided drill by the contra angle hand piece and for enabling revolving the guided drill by the contra angle hand piece, respectively.

Guided drill 100 further comprises a guide body 110 having an outer surface 112 geometrically confined to a cylinder having a diameter D1 so that the outer surface coincides with the cylinder at least along an areal section 114 thereof. The guided drill is thereby configured to slidingly revolve inside a guide sleeve (not shown) having a hollow cylindrical shape with an inner diameter D2 larger than D1, whereas the revolution axis 102 coincides with a symmetry axis of the guide sleeve. When the guided drill so slidingly revolves inside the guide sleeve, the guided drill is substantially constrained to displacements along the revolution axis.

Guided drill 100 further comprises a stopper 120 arranged between the shank 104 and the guide body 110. The stopper extends radially to a distance d from the revolution axis 102, d being greater than R1.

Guided drill 100 further comprises a blade portion 130 configured for drilling at a diameter D smaller than 2*R1. The blade portion is arranged next to the guide body, so that the guide body 110 is between the blade portion 130 and the stopper 120. The blade portion comprises four straight cutting edges, 132a-132d, tilted at an angle relative to the revolution axis, thereby being configured for conical drilling. Cutting edge 132a and cutting edge 132b are arranged opposite to one another and extend along the revolution axis up to a drilling edge 134. Cutting edges 132c and 132d are arranged opposite to one another and at a straight angle relative to cutting edges 132a and 132b. Cutting edges 132c and 132d are shorter than cutting edges 132a and 132b, thereby extending up to a distance from the drilling edge 134. Blade portion 130 further comprises reliefs 136, next to cutting edges 132 and drilling edge 134, for enhancing a quality of a drill and enhancing an endurance and a longevity of the guided drill.

The shank 104, the stopper 120, the guide body 110 and the blade portion 130 are integrally formed together from a hard alloy such as stainless still or titanium or an alloy thereof. The four cutting edges 132a-132d, the reliefs 136 and the hard alloy from which the blade portion 130 is formed, render the guided drill 100 a reusable drill. According to some embodiments, guided drill 100 is configured for more than 10 drills in a bone of a jaw wherein each such drill is carried out during an osteotomy procedure. According to some embodiments guided drill 100 is configured for more than 20 drills in a bone of a jaw. According to some embodiments guided drill 100 is even configured for more than 30 drills in a bone of a jaw.

Figure 2C:
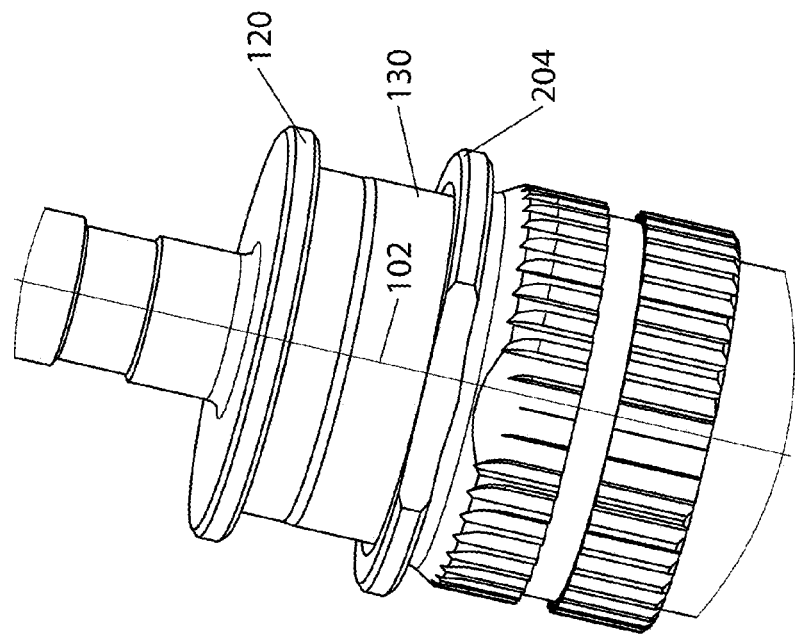
FIG. 2C schematically depicts the guided drill and guide sleeve of FIG. 2B in a blown-up view.
Figure 2B:
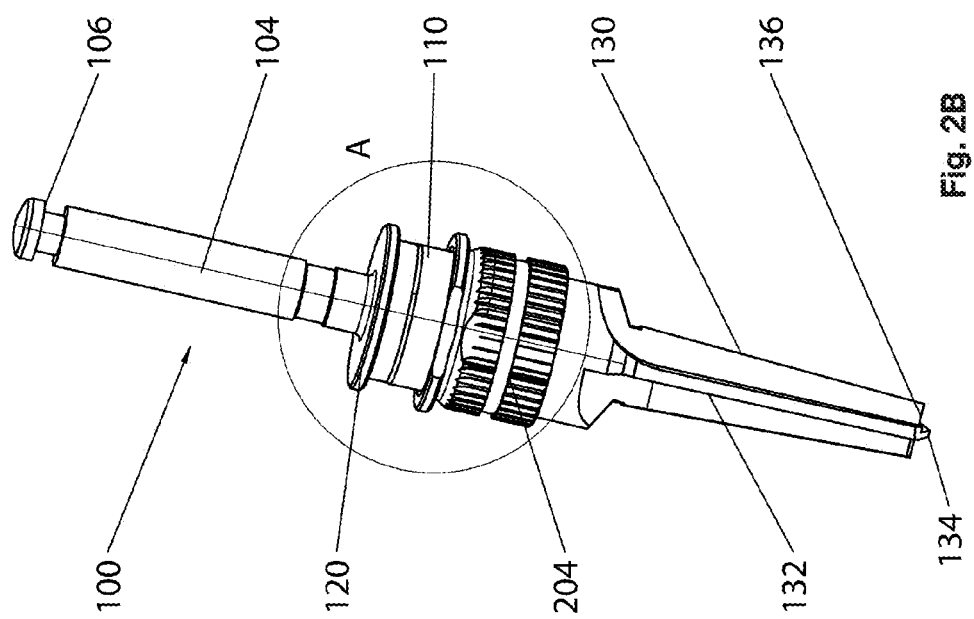
FIG. 2B schematically depicts the guided drill of FIG. 2A passing through a guide sleeve, in perspective.

FIG. 2B schematically depicts guided drill 100 in perspective, passing through a guide sleeve 204. As is further explained below, guide sleeve 204 is configured to guide guided drill 100 along a symmetry axis thereof while guided drill 100 revolves and drills. FIG. 2C schematically depicts guided drill 100 and guide sleeve 204 in a blown-up view of the encircled portion of FIG. 2B.

Figure 2D:
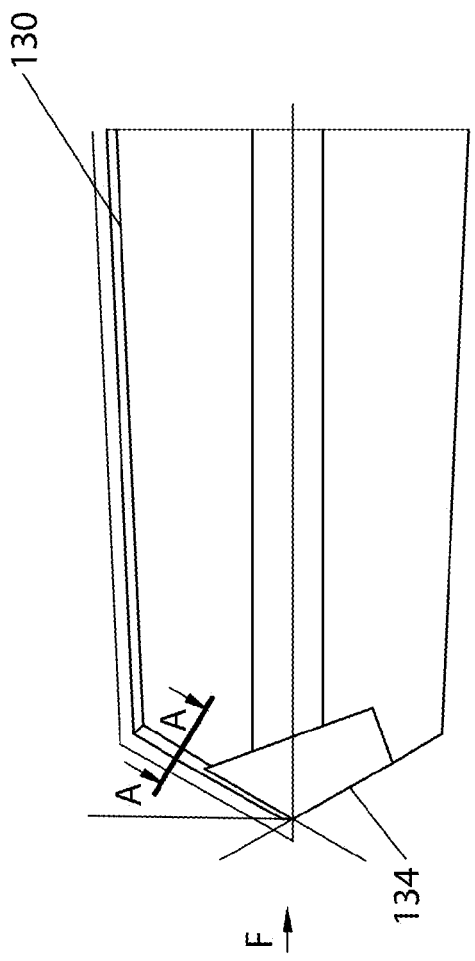
FIG. 2D depicts schematically a portion of the guided drill of FIG. 2A, comprising the drilling edge thereof.
Figure 2F:
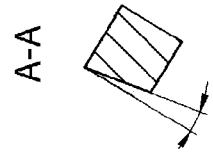
FIG. 2F depicts schematically a cross section view of the guided drill of FIG. 2A, showing a relief tilt angle.
Figure 2E:
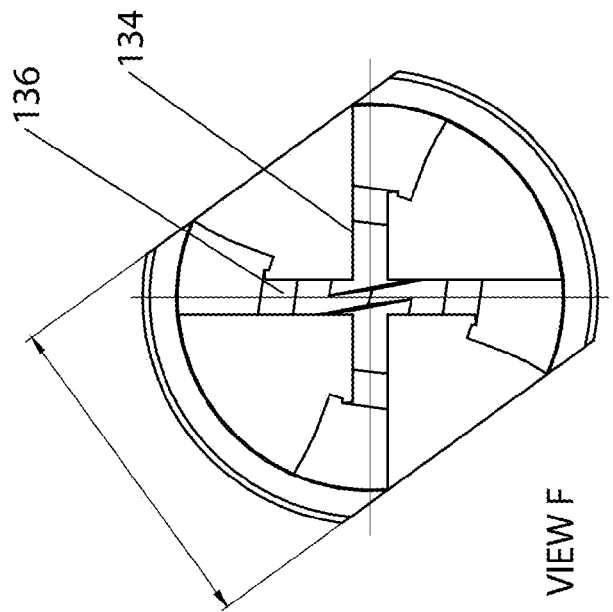
FIG. 2E depicts schematically the guided drill of FIG. 2A from "view F" defined in FIG. 2D, showing the drilling edges and reliefs thereof in detail.

FIG. 2D depicts schematically a portion of guided drill 100, comprising drilling edge 134 and relief 136 (not shown in this Figure). FIG. 2E depicts schematically guided drill 100 from "view F", wherein "view F" is defined in FIG. 2D, showing drilling edges 134 and reliefs 136 in detail. FIG. 2F depicts schematically cross section AA defined in FIG. 2D, showing in detail relief 136 in cross section. In some embodiments relief 136 in guided drill 100 is titled relative to drilling edge 134 at an angle of about 10 degrees.

FIG. 2G schematically depicts, in a perspective view, a guided drill 150 according to an aspect of some embodiments, passing through guide sleeve 204 as described above. Guided drill 150 is different from guided drill 100 in that guided drill 150 comprises a blade portion 160 comprising two spiral cutting edges 162 (instead of blade portion 130 in guided drill 100, which comprises four straight cutting edges 132). Blade portion 160 further comprises a drilling edge 164 and reliefs 166 and 168 next to cutting edges 162 and drilling edge 164 as is known in the art, for enhancing a quality of a drill and enhancing an endurance and a longevity of the guided drill.

FIG. 2H schematically depicts guided drill 150 and guide sleeve 204 in a front view. FIG. 2I schematically depicts guided drill 150 and guide sleeve 204 in a blown-up, cross-section view of the encircled portion of FIG. 2H.

Figure 2J:
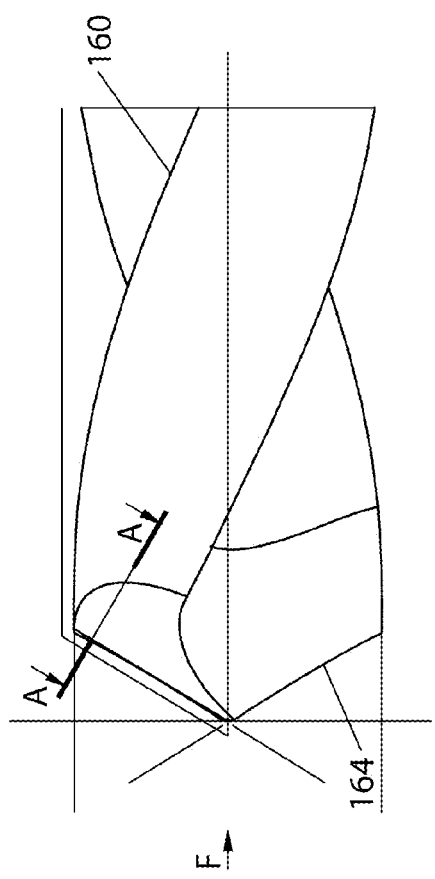
FIG. 2J depicts schematically a portion of the guided drill of FIG. 2G, comprising the drilling edge thereof.
Figure 2L:
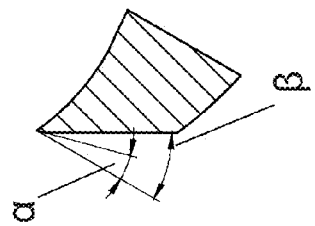
FIG. 2L depicts schematically a cross section view of the guided drill of FIG. 2G, showing reliefs tilt angles.
Figure 2K:
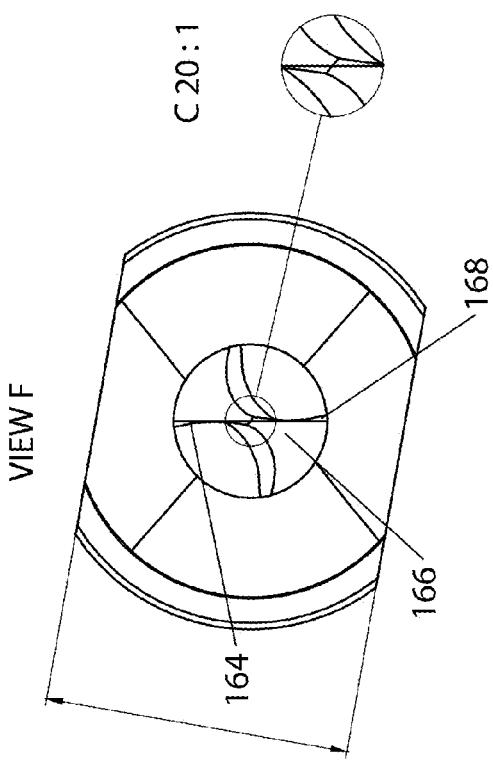
FIG. 2K depicts schematically the guided drill of FIG. 2G from "view F" defined in FIG. 2J, showing the drilling edges and reliefs thereof in detail.

FIG. 2J depicts schematically a portion of guided drill 150, comprising drilling edge 164 and relief 166 and 168 (not shown in this Figure). FIG. 2K depicts schematically guided drill 150 from "view F", wherein "view F" is defined in FIG. 2J, showing drilling edges 164 and reliefs 166 and 168 in detail. FIG. 2L depicts schematically cross section AA defined in FIG. 2J, showing in detail reliefs 166 and 168 in cross section. In some embodiments relief 166 in guided drill 150 is titled relative to drilling edge 164 at an angle alpha of about 15 degrees, and relief 168 is titled relative to drilling edge 164 at an angle beta of about 30 degrees.

FIGS. 3A-3C schematically depict an embodiment of a surgical template 200 according to an aspect of the invention, in a perspective view, in top view and in an exploded view, respectively. The surgical template is constructed to mechanically fit to teeth in an upper jaw or in a lower jaw of a specific patient, substantially as described above regarding surgical template 40. When the surgical template is attached to the teeth of the patient in a pre-defined mutual orientation between the teeth and the surgical template, the surgical template grips onto the teeth, so that the surgical template is substantially fixed relative to the teeth. Surgical template 200 comprises cylindrical housings 202a-202c configured to house guide sleeves therein as is described herein. Surgical template 200 further comprises guide sleeves 204a-204c, made of hard metal such as stainless steel or titanium, wherein guide sleeves 204a-204c are attached to the surgical template, e.g. by gluing, inside cylindrical housings 202a-202c, respectively. Guide sleeves 204 are formed as hollow cylinders, all having an identical inner radius of R2, larger than the radius R1 of the guide body 110 of guided drill 100, thereby allowing passage of blade portion 130 and of guide body 100 therethrough. The constant inner radius R2 of guide sleeve 204 is yet smaller than the distance d related to stopper 120 of the guided drill, so that stopper 120 cannot pass through the guide sleeve. According to some embodiments, R2 may be larger than R1 by about 0.01 mm to about 0.1 mm. According to some embodiments R2 may be larger than R1 by about 0.02 mm to about 0.08 mm. According to some embodiments R2 may be larger than R1 by about 0.03 mm to about 0.06 mm. According to some embodiments R2 may be larger than R1 so that a guide body of a guided drill such as guided drill 100 is enabled to slidingly revolve inside guide sleeve 204 while the revolution axis 102 substantially coincides with a symmetry axis of the guide sleeve, and the guided drill is constrained to displacements substantially along the revolution axis.

The cylindrical housings 202 and thereby the guide sleeves 204 are positioned, located and oriented so that when the surgical template is attached to the patient's teeth, a guided drill passing therethrough is directed towards an osteotomy site in the patient's jaw. During an osteotomy procedure a guided drill, being revolved by a contra angle hand piece, is passed through one of the guide sleeves so that the guide body of the guide drill is substantially inside the guide sleeve and slidingly revolves therein. Drilling is carried out by advancing the guided drill through the guide sleeve into the bone, as the guide sleeve guides the guided drill in a pre-defined direction. According to some embodiments, the distance d related to the stopper of the guided drill is larger than R2. Therefore, advancement of the guided drill into the bone while drilling is carried out until the stopper of the guided drill contacts the guide sleeve. The cylindrical housings 202 and thereby the guide sleeves 204 are positioned, located and oriented so that when the surgical template is attached to the patient's teeth, a guided drill passing therethrough can drill a hole in the bone of the jaw up to a pre-defined depth, the depth of the hole is set by the position of the guide sleeve relative to the osteotomy site and by a length of the guided drill, specifically, by a distance between the stopper and the drilling edge of the guided drill.

FIG. 4 schematically depicts series 400a, 400b and 400c of guided drills such as described above in FIG. 2A. Series 400a comprises guided drills 402a-402e, all having an identical drilling diameter (suitable for e.g. a 3.75 mm diameter implant) and drilling lengths of 6 mm, 8 mm, 10 mm 11.5 mm and 13 mm, in successive guided drills 402a-402e, respectively. Likewise, Series 400b comprises guided drills 404a-404e, all having an identical drilling diameter (suitable for e.g. a 5 mm diameter implant) and drilling lengths similar to the respective drilling lengths of the guided drills of series 4001a, namely 6 mm, 8 mm, 10 mm 11.5 mm and 13 mm, in successive guided drills 404a-404e, respectively. Series 400c comprises guided drills 402a and 404a, both having an identical drilling length of 6 mm and successive drilling diameters, suitable for e.g. a 3.5 mm and for a 5 mm diameter implant, respectively.

All the guided drill in series 400a, 400b and 400c have an identical radius R1 associated with the guide body thereof. Thus, a series of guided drills such as series 400a-400c enable a user of the series of guided drills such as a maxillofacial surgeon, to perform efficiently, using the series, at least a part of a guided osteotomy procedure for a dental implant, using a guide sleeve as described above. According to some exemplary embodiments, the surgeon, during a procedure taken to drill a hole for a 3.5 mm diameter implant, may use guided drill 402a, thereby drilling a hole of about 6 mm length. Then the surgeon may use a successive guided drill 402b, having a same drilling diameter as the former guided drill 402a, and a length of 8 mm, thereby correspondingly increasing the depth of the drilled hole. At a next step the surgeon may further continue and use a yet successive guided drill such as guided drill 402c to further increase the depth of the drilled hole to about 10 mm.

Additionally or alternatively, the surgeon may use series 400c during an osteotomy procedure, and, following using guided drill 402a as described above, may use the successive guided drill in the series, guided drill 404a, thereby increasing the diameter of the drilled hole. It is noted that because the radius R1 in all the guided drills in the series is the same, the surgeon can replace a first guided drill in the contra angle hand piece with a successive guided drill from the series and continue the osteotomy procedure through the same guide sleeve without being required to replace additional parts or components and without being required to modify or to tune a tunable part and without being required to be assisted by an assistant for the drilling procedure. Moreover, the surgeon may select, during the osteotomy procedure, a drilling sequence comprising a series of guided drills each having a different combination of a drilling diameter and a drilling length, and use the guided drills in the series successively, to carry out the procedure. Such a particular drilling sequence and an associated osteotomy procedure may be selected for example according to data collected during the procedure, such as anatomic data of the patient, as is further explained and detailed herein.

FIG. 5A schematically depicts a surgical kit 500 for assisting in drilling a hole in a bone of a patient's jaw. The kit comprises a container 510, having a cover 512 configured to cover a content of the container when in a closed state (not shown in this Figure), and whereas the content of the container is visible and accessible to a user when the cover is in an open state, as is depicted in FIG. 5.

Figure 5B:
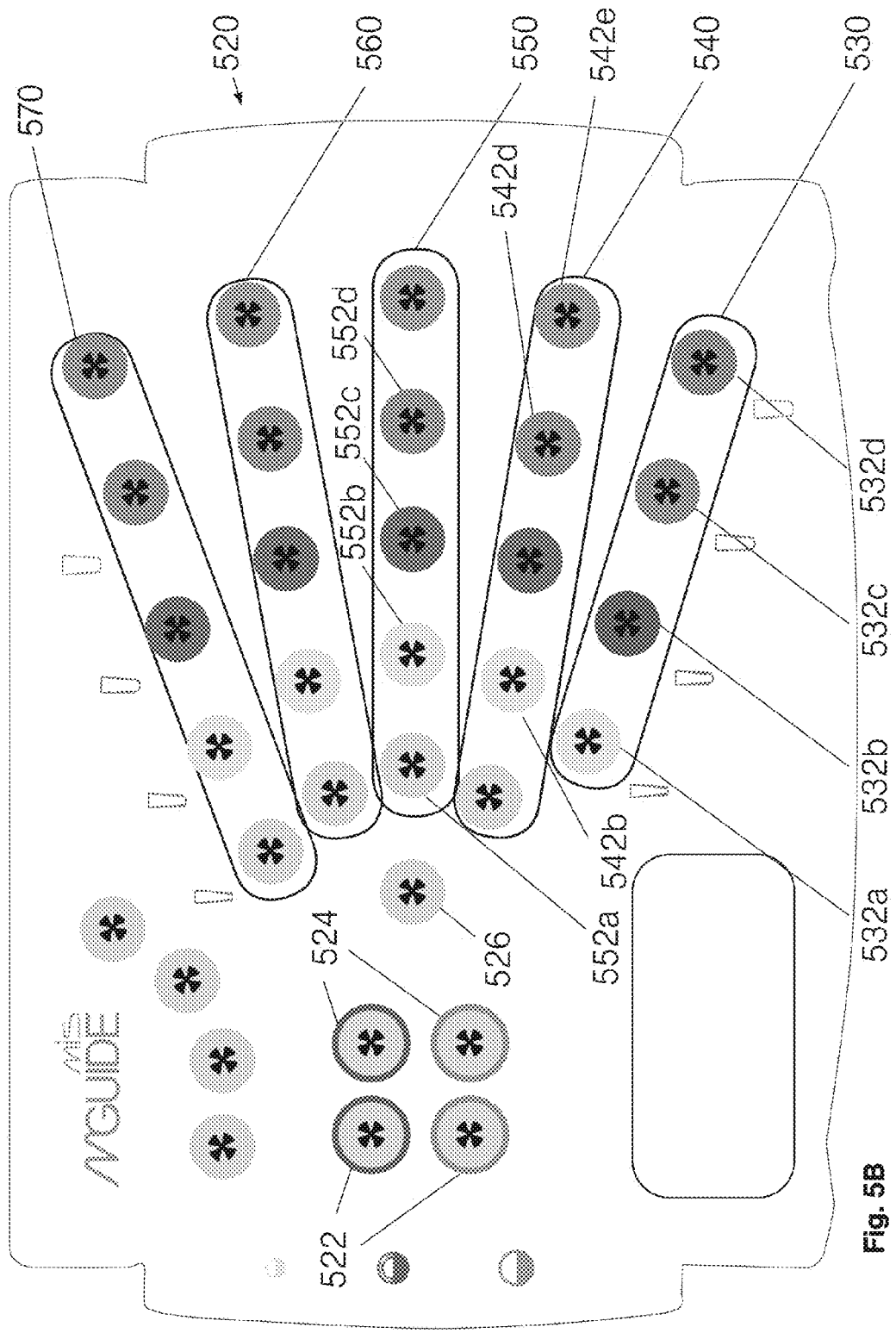
FIG. 5B schematically depicts the array of FIG. 5A in top view.

Kit 500 further comprises series of guided drills as described above wherein each guided drill in a series has a unique combination of drilling diameter and drilling length. The series of guided drills are arranged in the container in an array 520. FIG. 5B schematically depicts array 520 in top view. Next to each guided drill in the array, having a specified drilling diameter and a specified drilling length, is disposed another guided drill having a successive drilling diameter or a successive drilling length in the series of guided drills. "Successive" herein means a next value in a series, when the series is arranged in a descending order or in an ascending order.

For example, series 530 comprises guided drills 532a-532d, all having a same drilling length of 6 mm and drilling diameters in the range of 2.2 mm (3.2 mm) and 4.1 mm (4.9 mm). It is noted that the guided drills are conical and therefore have a non-constant drilling diameter. For example, guided drill 532a has a drilling diameter of 2.2 mm near the drilling edge of the blade portion (and a drilling diameter of 3.2 mm near the guide body). The next guided drill in the series, guided drill 532b, has a successive drilling diameter of 2.8 mm near the drilling edge of the blade portion (and a drilling diameter of 3.6 mm near the guide body). Series 540 comprises guided drills 542b-542e, all having a same drilling length of 8 mm and drilling diameters in the range of 2.2 mm (3.2 mm) and 4.1 mm (4.9 mm). For example, guided drill 542d has a drilling diameter of 3.3 mm near the drilling edge of the blade portion (and a drilling diameter of 4.1 mm near the guide body). The next guided drill in the series, guided drill 542e, has a successive drilling diameter of 4.1 mm near the drilling edge of the blade portion (and a drilling diameter of 4.9 mm near the guide body), and so on. Additionally to guided drills in array 520, kit 500 may comprise additional drills such as tissue punch 522, bone mill 524 and starter guided drill 526.

Figure 5C:
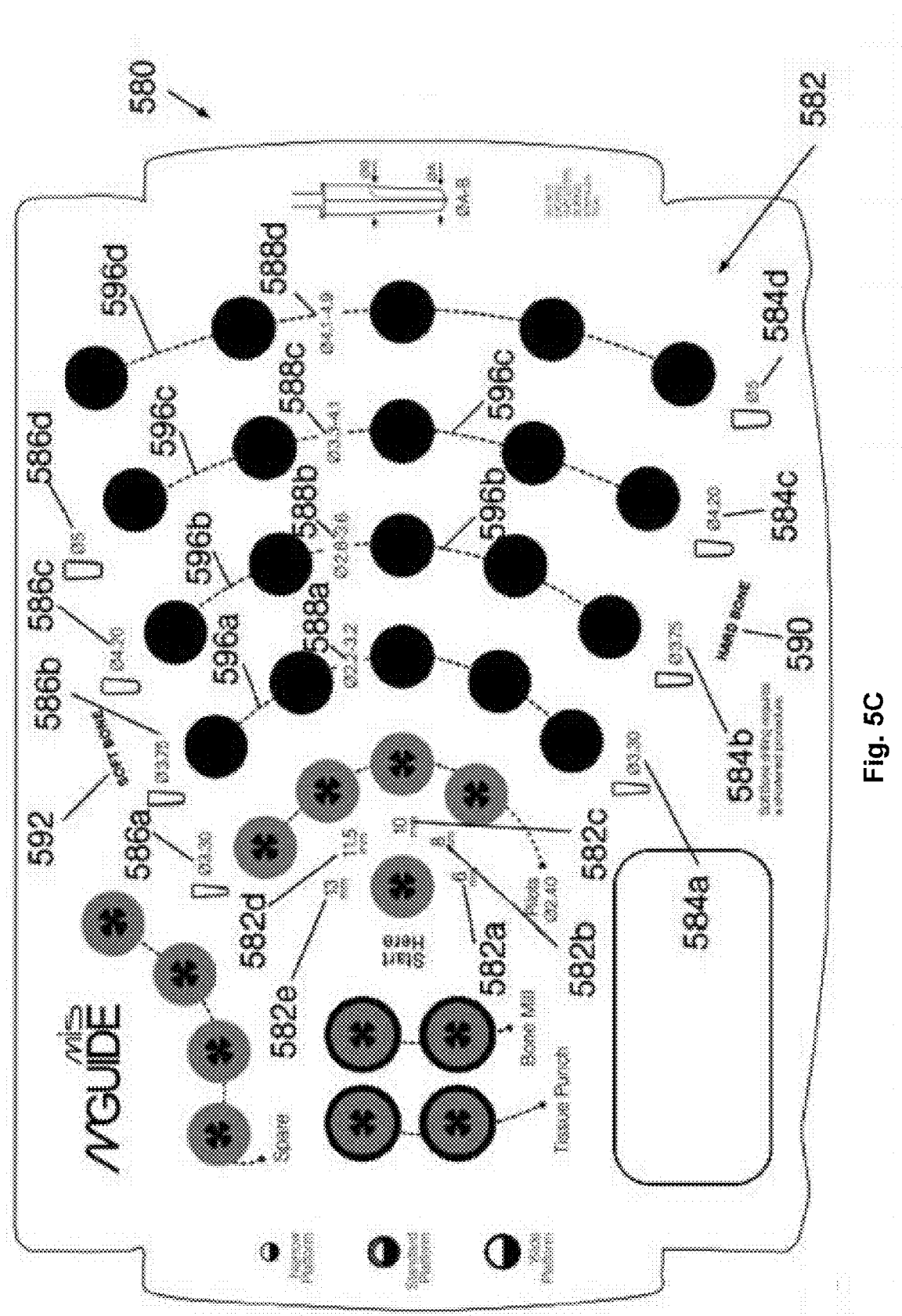
FIG. 5C schematically depicts the chart of FIG. 5A.

Kit 500 further comprises a chart 580, depicted schematically in FIG. 5C, the chart comprising a map 582 of the array 520, and further comprising graphical indications as is further explained below. The graphical indications are configured to indicate to a user a suggested order of sequentially using a series or a sub-series of the guided drills to perform a part of osteotomy procedure and obtain a hole, having a prescribed diameter and a prescribed length, for a dental implant.

Chart 580 comprises length indications 582a-582e, disposed next to series 530-570, respectively. Each length indication indicates the drilling length of the guided drills in the respective series. For example, indication 582a of 6 mm indicates that the drilling length of guided drills in series 530 is 6 mm. Indication 582b of 8 mm indicates that the drilling length of guided drills in series 540 is 8 mm, and so on.

Next to series 530 there are diameter indications 584a-584d, whereas next to each diameter indication 584b-584d there is a symbol of an implant. The chart further comprises a note 590 next to diameter indications 584a-584d, reading "HARD BONE". Thus, diameter indications 584a-584d indicate to a user what guided drill should be used to insert an implant with a specified diameter in a hard bone. Likewise, next to series 570 there are diameter indications 586a-586d, whereas next to each diameter indication 586b-586d there is a symbol of an implant. The chart further comprises a note 592 next to diameter indications 586a-586d, reading "SOFT BONE". Thus, diameter indications 586a-586d indicate to a user what guided drill should be used to insert an implant with a specified diameter in a soft bone.

Chart 580 further comprises dashed lines 596a-596d indicating to a user series of guided drills having a same drilling diameter (and successive drilling lengths). The chart further comprises diameter indications 588a-588d, disposed between series 550 and series 560. Diameter indications 588a-588d indicate the actual drilling diameters of the guided drills in a series of guided drills along a particular dashed line 596.

Figure 6:
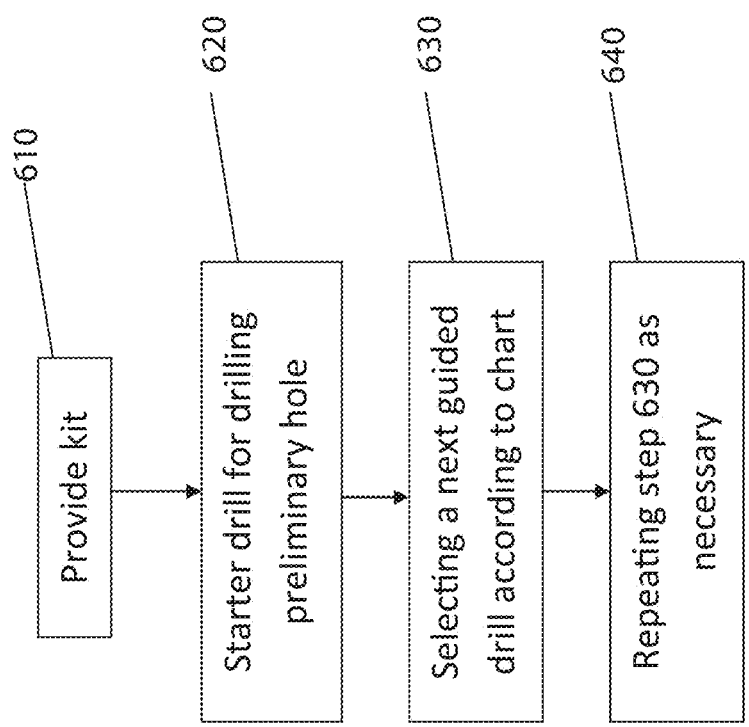
FIG. 6 schematically depicts an embodiment of a method for carrying out a part of an osteotomy procedure, using the kit of FIG. 5A.

According to an aspect of some embodiments, there is provided a method for carrying out a part of an osteotomy procedure, using the kit 500, as schematically depicted in FIG. 6. All drilling described herein are performed using a surgical template, having a guide sleeve. The guide sleeve is used to guide the drilling drill to the osteotomy site, and to determine the depth of the hole drilled in the bone, as explained and described above.

Preliminary steps that may precede methods disclosed herein may include gingival puncturing using tissue punch 522, for exposing the bone in the osteotomy site, and bone milling, using bone mill 524, for preparing the exposed bone for drilling. Following a step 610 of providing a kit for osteotomy procedure as is disclosed herein, a step 620 may comprise using starter guided drill 526 to perform a preliminary hole in the bone. Starter guided drill 526 has a relatively short drilling length of about 6 mm and a cylindrical drilling cross section with a diameter of about 2.4 mm. Drilling a first hole in the bone using starter guided drill 526 provides a preliminary hole in the bone. The preliminary hole may, in some cases, be deepened and/or broadened in following steps of the osteotomy procedure using other guided drills from the kit. Drilling the first hole in the bone using starter guided drill 526 may further provide the user with anatomic data of the patient, the jaw and the bone therein. Such anatomic data may include for example bone hardness, which may be sensed by the surgeon during drilling the preliminary hole. As explained above, data on bone hardness may have a significant effect on the diameter of the drilled hole, for a pre-determined implant, because, generally, an implant having a specific diameter requires a narrower hole in a soft bone compared to a hole in a hard bone. Moreover, valid and accurate data regarding bone hardness, specifically at the exact osteotomy site, may not be available from X-ray images. Therefore, an impression of the surgeon during the surgical procedure, and consequent decisions for using a specific drill (optionally different from a pre-planned drill), may be important for a successful completion of the procedure. Other data collected during the preliminary drilling may comprise images taken using an X-ray machine or using a different technology after the preliminary drilling for inspecting the actual position of the drilled hole in the bone. Such images, or other data, may be considered for deciding on a preferred depth of the hole, a decision that elicits a choice of a preferred guided drill to be used next.

Following step 620, the method may comprise a step 630 of selecting a next guided drill according to the chart of the surgical kit, and drilling a next drill in the bone of a patient's jaw. Step 630 may be preceded, in some embodiments, by a step of collecting anatomic data of the patient, and by a step of considering the anatomic for selecting the next guided drill. According to some embodiments the anatomic data may comprises data on bone hardness, collected e.g. during the preliminary drill as described above.

Following step 630 the method may comprise a step 640 of repeating step 630, wherein in each instance of performing step 630 a successive guided drill is selected to be used, until a hole is obtained with a desired depth and diameter.

For example, according to some embodiments a part of an osteotomy procedure according to the teachings herein may thus comprise obtaining a pre-planned program for inserting a 10 mm length, 4.2 mm diameter implant at a prescribed osteotomy site. A next step may comprise drilling a preliminary hole using the starter guided drill 526 thereby obtaining data regarding bone hardness and/or bone density at the osteotomy site. The surgeon may then select series 550 (in FIG. 5B) and use sequentially guided drills 552a, 552b and 552c to subsequently obtain a hole of a diameter between 2.8-3.6 mm. If the surgeon finds that the bone is soft, the obtained hole is suitable, and no more drilling has to be done, according to indication 586c (FIG. 5C). If, however, the bone is hard, one more drilling should be performed, to obtain a hole at a diameter between 3.3-4.1 mm, according to indication 584c (FIG. 5C). Thus, by following the chart of the surgery kit, the surgeon may easily and quickly select and use the desired drills for obtaining an hole, optimized for the implant dimensions and for the patient, the jaw and the bone thereof.

According to some embodiments, following step 620, guided drills are selected from a series of guided drills having a same length (e.g. series 550 in FIG. 5B), so that each drilling may broaden the drilled hole, but does not substantially increase the drilled hole depth.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

Section headings are used herein to ease understanding of the specification and should not be construed as necessarily limiting.

The invention claimed is:

1. A guided drilling system for osteotomy for a dental implant using a guide sleeve, said guide sleeve having a hollow cylindrical shape with an inner radius R2, comprising:
    a plurality of guided drills, wherein each of the plurality of guided drills comprises:
        a shank configured to be releasably mechanically associated with a contra angle hand piece, said contra angle hand piece being configured to revolve the guided drill around a revolution axis;
        a guide body having an outer surface geometrically confined to a cylinder having a radius R1 smaller than R2 so that said outer surface coincides with the cylinder at least along an areal section thereof, the guided drill is thereby configured to slidingly revolve inside said guide sleeve, whereas said revolution axis coincides with a symmetry axis of said guide sleeve, so that the guided drill is constrained to displacements substantially along said revolution axis;
        a stopper arranged between said shank and said guide body, said stopper extending radially to a distance greater than R1 from said revolution axis, and
        a blade portion configured for drilling at a diameter smaller than 2*R1, said blade portion arranged next to said guide body, so that said guide body is between said blade portion and said stopper;
    wherein said shank, said stopper, said guide body and said blade portion are integrally formed together from a hard alloy, and wherein said radius R1 is uniform across each of the plurality of guided drills.

2. The guided drilling system of claim 1, further comprising:
    a surgical template constructed to mechanically fit to teeth in an upper jaw or in a lower jaw of a specific patient so that said surgical template, when attached to said teeth in a pre-defined mutual orientation between said teeth and said surgical template, said surgical template grips onto said teeth, and wherein said surgical template comprises a guide sleeve having a hollow cylindrical shape with an inner radius R2, said guide sleeve being oriented, when said surgical template is attached to a patient's teeth, so as to enable passage of any one of the plurality of guided drills therethrough towards an osteotomy site in the patient's jaw, and said guide sleeve is configured to guide any one of the plurality of guided drills, having said guide body confined within a radius R1 smaller than R2, towards said osteotomy site.

3. The guided drilling system of claim 1, wherein the plurality of guided drills comprises a series of guided drills.

4. The guided drilling system of claim 3, wherein each said guide body of each guided drill in the series of guided drills is geometrically confined to a same cylinder with a same radius R1, and wherein each guided drill in the series provides a combination of a drilling diameter and a drilling length different from a combination of a drilling diameter and a drilling length provided by another guided drill in the series, the series is thereby configured to enable a user of the series of guided drills to perform, using the series, osteotomy for a dental implant at a drilling diameter and a drilling length which are decided upon by the user during the osteotomy procedure.

5. The guided drilling system of claim 3, further comprising:
    a surgical template constructed to mechanically fit to teeth in an upper jaw or in a lower jaw of a specific patient so that said surgical template, when attached to said teeth in a pre-defined mutual orientation between said teeth and said surgical template, said surgical template grips onto said teeth, and wherein said surgical template comprises a guide sleeve having a hollow cylindrical shape with an inner radius R2, said guide sleeve being oriented, when said surgical template is attached to a patient's teeth, so as to enable passage of any one of the plurality of guided drills therethrough towards an osteotomy site in the patient's jaw, and said guide sleeve is configured to guide any one of the plurality of guided drills, having said guide body confined within a radius R1 smaller than R2, towards said osteotomy site; and wherein each said guide body of each guided drill in the series of guided drills is geometrically confined to a same cylinder with a same radius R1, and wherein each guided drill in the series provides a combination of a drilling diameter and a drilling length different from a combination of a drilling diameter and a drilling length provided by another guided drill in the series, the series is thereby configured to enable a user of the series of guided drills to perform, using the series, osteotomy for a dental implant at a drilling diameter and a drilling length which are decided upon by the user during the osteotomy procedure.

6. A surgical kit for containing the guided drilling system of claim 1, wherein:
the plurality of guided drills comprises a series of guided drills; and
the guided drilling system further comprises:
a container configured to contain at least said series of guided drills, and said container has an open state wherein said series of guided drills are visible and accessible to a user, and wherein, in said open state, said series of guided drills are arranged in an array according to at least one of a drilling diameter and a drilling length of each guided drill so that next to each guided drill in said array, having a specified drilling diameter and a specified drilling length, is disposed another guided drill having a successive drilling diameter or a successive drilling length in said series of guided drills, and
a chart comprising a map of said array and graphical indications configured to indicate to a user of the surgical kit a suggested order of sequentially using a sub-series of said series of guided drills to perform a part of osteotomy procedure and obtain a hole, having a prescribed diameter and a prescribed length, for a dental implant;
wherein each of said sub-series flares away from other sub-series when advancing in said successive drilling diameter or in said successive drilling length.

7. A method of osteotomy for a dental implant using a guide sleeve, said guide sleeve having a hollow cylindrical shape with an inner radius R2, the method comprising:
a. providing a surgical kit having a plurality of guided drills;
b. following a chart of the surgical kit, selecting a first guided drill from the plurality of guided drills and drilling a first drill in an osteotomy site in a bone of a patient's jaw;
c. according to the chart of the surgical kit, selecting a next guided drill from the plurality of guided drills and drilling a next drill in a bone of a patient's jaw; and
d. repeating step (c) as many times as desired by a user of the surgical kit;

wherein each of the plurality of guided drills comprises:
a shank configured to be releasably mechanically associated with a contra angle hand piece, said contra angle hand piece being configured to revolve the guided drill around a revolution axis;
a guide body having an outer surface geometrically confined to a cylinder having a radius R1 smaller than R2 so that said outer surface coincides with the cylinder at least along an areal section thereof, the guided drill is thereby configured to slidingly revolve inside said guide sleeve, whereas said revolution axis coincides with a symmetry axis of said guide sleeve, so that the guided drill is constrained to displacements substantially along said revolution axis;
a stopper arranged between said shank and said guide body, said stopper extending radially to a distance greater than R1 from said revolution axis, and
a blade portion configured for drilling at a diameter smaller than 2*R1, said blade portion arranged next to said guide body, so that said guide body is between said blade portion and said stopper;
wherein said shank, said stopper, said guide body and said blade portion are integrally formed together from a hard alloy, and wherein said radius R1 is uniform across each of the plurality of guided drills.

8. The method of claim 7, wherein the surgical kit further comprises:
a series of guided drills, wherein each said guide body of each guided drill in the series of guided drills is geometrically confined to a same cylinder with a same radius R1, and wherein each guided drill in the series provides a combination of a drilling diameter and a drilling length different from a combination of a drilling diameter and a drilling length provided by another guided drill in the series, the series is thereby configured to enable a user of the series of guided drills to perform, using the series, osteotomy for a dental implant at a drilling diameter and a drilling length which are decided upon by the user during the osteotomy procedure;
a container configured to contain at least said series of guided drills, and said container has an open state wherein said series of guided drills are visible and accessible to a user, and wherein, in said open state, said series of guided drills are arranged in an array according to at least one of said drilling diameter and drilling length of each guided drill so that next to each guided drill in said array, having a specified drilling diameter and a specified drilling length, is disposed another guided drill having a successive drilling diameter or a successive drilling length in said series of guided drills, and
wherein the chart comprises a map of said array and graphical indications configured to indicate to a user of the surgical kit a suggested order of sequentially using a sub-series of said series of guided drills to perform a part procedure and obtain a hole, having a prescribed diameter and a prescribed length, for a dental implant.

9. The method of claim 7 further comprising:
providing a surgical template configured to fit and attach to teeth of the patient, wherein a guide sleeve of the surgical template is oriented so as to guide a guided drill towards the osteotomy site, and passing a drilling guided drill through the guide sleeve of the surgical template so that during drilling in steps (b) and (c), the guide body of the guided drill slidingly revolves inside the guide sleeve, thereby guiding the guided drills to drill in the osteotomy site, to a prescribed drilling depth.

10. The method of claim 9, wherein the surgical template further comprises:
a surgical template constructed to mechanically fit to teeth in an upper jaw or in a lower jaw of a specific patient so that said surgical template, when attached to said teeth in a pre-defined mutual orientation between said teeth and said surgical template, said surgical template grips onto said teeth, and wherein said surgical template comprises a guide sleeve having a hollow cylindrical shape with an inner radius R2, said guide sleeve being oriented, when said surgical template is attached to a patient's teeth, so as to enable passage of any one of the plurality of guided drills therethrough towards an osteotomy site in the patient's jaw, and said guide sleeve is configured to guide any one of the plurality of guided drills, having said guide body confined within a radius R1 smaller than R2, towards said osteotomy site.

11. The method of claim 7, further comprising:
collecting anatomic data of the patient following step (b), and
considering the anatomic data for selecting a next guided drill in step (c).

12. The method of claim 11 wherein the anatomic data comprises bone hardness and/or bone density.

13. An osteotomy set for a dental implant using a guide sleeve, said guide sleeve having a hollow cylindrical shape with an inner radius R2, comprising:
a plurality of guided drills, wherein each of the plurality of guided drills comprises:
a shank configured to be releasably mechanically associated with a contra angle hand piece, said contra angle hand piece being configured to revolve the guided drill around a revolution axis;
a guide body having at least a portion of an outer surface geometrically confined to a cylinder having a radius R1 smaller than R2 so that said outer surface coincides with the cylinder at least along an areal section thereof, the guided drill is thereby configured to slidingly revolve inside said guide sleeve;
a stopper arranged between said shank and said guide body, said stopper extending radially to a distance greater than R1 from said revolution axis, and
a blade portion configured for drilling at a diameter smaller than 2*R1, said blade portion arranged next to said guide body, so that said guide body is between said blade portion and said stopper;
wherein said shank, said stopper, said guide body and said blade portion are integrally formed together from a hard alloy, and wherein said radius R1 is uniform across each of the plurality of guided drills.

14. The osteotomy set of claim 13, further comprising:
a surgical template constructed to mechanically fit to teeth in an upper jaw or in a lower jaw of a specific patient; and
a guide sleeve having a hollow cylindrical shape with an inner radius R2.

15. The osteotomy set of claim 14, wherein the guide sleeve is oriented, when said surgical template is attached to a patient's teeth, so as to enable passage of any one of the plurality of guided drills therethrough towards an osteotomy site in the patient's jaw, and said guide sleeve is configured to guide any one of the plurality of guided drills, having said guide body confined within a radius R1 smaller than R2, towards said osteotomy site.

16. The osteotomy set of claim 14, wherein the guide sleeve of the surgical template is oriented so as to guide the guided drill towards the osteotomy site.

17. The osteotomy set of claim 13, wherein the plurality of guided drills comprises a series of guided drills.

18. The osteotomy set of claim 17, wherein each said guide body of each guided drill in the series of guided drills is geometrically confined to a same cylinder with a same radius R1, and wherein each guided drill in the series provides a combination of a drilling diameter and a drilling length different from a combination of a drilling diameter and a drilling length provided by another guided drill in the series.

19. The osteotomy set of claim 17, wherein each guided drill in the series provides a combination of a drilling diameter and a drilling length different from a combination of a drilling diameter and a drilling length provided by another guided drill in the series.

20. The osteotomy set of claim 17, further comprising:
a container configured to contain at least said series of guided drills, and said container has an open state wherein said series of guided drills are visible and accessible to a user, and wherein, in said open state, said series of guided drills are arranged in an array according to at least one of said drilling diameter and drilling length of each guided drill so that next to each guided drill in said array, having a specified drilling diameter and a specified drilling length, is disposed another guided drill having a successive drilling diameter or a successive drilling length in said series of guided drills, and
a chart comprising a map of said array and graphical indications configured to indicate to a user of the surgical kit a suggested order of sequentially using a sub-series of said series of guided drills to perform a part of osteotomy procedure and obtain a hole, having a prescribed diameter and a prescribed length, for a dental implant.

21. The method of claim 8 wherein each of said sub-series flares away from other sub-series when advancing in said successive drilling diameter or in said successive drilling length.

* * * * *